US00PP14540P29

(12) United States Plant Patent
Colfer

(10) Patent No.: US PP14,540 P2
(45) Date of Patent: Feb. 17, 2004

(54) ARTICHOKE PLANT NAMED 'PS-MSC0006'

(50) Latin Name: *Cynara scolymus L.*
Varietal Denomination: PS-MSC0006

(75) Inventor: William J. Colfer, Aptos, CA (US)

(73) Assignee: Seed Research Services, LLC, Salinas, CA (US)

( * ) Notice: Subject to any disclaimer, the term of this patent is extended or adjusted under 35 U.S.C. 154(b) by 0 days.

(21) Appl. No.: 10/251,980

(22) Filed: Sep. 23, 2002

(51) Int. Cl.[7] ..... A01H 5/00
(52) U.S. Cl. ..... Plt./258
(58) Field of Search ..... Plt./258

(56) References Cited

U.S. PATENT DOCUMENTS

PP12,210 P2 * 11/2001 Colfer ..... Plt./258

* cited by examiner

*Primary Examiner*—Bruce R. Campell
*Assistant Examiner*—W C Haas
(74) *Attorney, Agent, or Firm*—Foley & Lardner

(57) ABSTRACT

A new and distinct cultivar of artichoke plant named 'PS-MSC0006', characterized by male sterility, fleshiness of bracts, fleshiness of hearts, uniformity of head shapes, compace, reduced plant height, and reduced spinosity on bracts.

3 Drawing Sheets

Latin name of the genus and species of the plant claimed: *Cynara scolymus* L.
Variety denomination: PS-MSC0006.

BACKGROUND OF THE INVENTION

The present invention comprises a new and distinct cultivar of artichoke plant, botanically known as *Cynara scolymus* L. and herein referred to by the cultivar name 'PS-MSC0006'.

*Cynara scolymus* L., commonly known as Globe artichoke, is a thistle-like perennial herb and is a member of the family Asteraceae. Globe artichokes comprise leaves which are pinnately lobed but primarily spineless, globose capitula composed of overlapping layers of large involucral bracts, and receptacles which are enlarged and fleshy. Globe artichoke plants may be propagated by division and are essentially grown for the production of the immature flower heads, which are considered as vegetable delicacies. Fresh artichokes may be steamed or boiled, after which the fleshy receptacle, inner and outer bracts, and parts of the floral stem may be eaten.

The new cultivar is a product of a planned breeding program carried out by the inventor, William J. Colfer at Chowchilla, Calif. in 1997. The female parent is CTC6 (seed parent). The male parent is an unknown cultivar selected from an open-pollinated breeding plot. The new cultivar was discovered from the progeny of the stated cross by William J. Colfer and was asexually propagated for the first time in 1997 in Watsonville, Calif.

Asexual propagation by division has demonstrated the stability of the combination of characteristics of the new cultivar from generation to generation.

BRIEF DESCRIPTION OF THE DRAWINGS

The accompanying photographic drawings show fruit and leaves from a typical specimen plant of 'PS-MSC0006', with color being depicted as possible with illustrations of this type.

The first drawing is a side-view of the fruit and foliage of 'PS-MSC0006'.

The second drawing is a side-view of the fruit showing its physical dimensions.

The third drawing is a side-view showing a vertical cross-section of the fruit.

BRIEF SUMMARY OF THE INVENTION

The new cultivar has not been observed under all possible environmental conditions. The phenotype may vary with variations in environment, such as temperature, light intensity and day length, without any change in the genotype of the cultivar.

In the following description, holding quality was measured by the physical appearance of the harvested heads. This includes the heads appearance following 3, 7 and 10 day storage periods in a cold storage room held at 34 (degrees Fahrenheit). Head exterior (oxidation) was observed at each of the three observation points. Browning and blackening of plant tissue was evaluated as light, moderate and extreme. Juiciness was measured by observing exudate and rated as absent, moderate or excessive. Overall storage response was measured by observing heads following 3, 7 and 10 day cold storage periods. These observations concentrated on visible color variability and/or presence of lesions or other cosmetic anomalies. Leaf ratio (L/W) was determined by dividing representative leaf sample length measurements by representative leaf sample width measurements. Finally, head response to (weather) was determined by observing the heads at maturity. These field observations focus on presence or absence of bronzing, necrotic and chlorotic lesions or any abiotic response to environmental conditions. These data are reported as the possible causal event(s) and then describe the detailed head and plant responses.

It should be noted that these data were collected from first year tissue culture outplants. These date are subject to change in the plant's future growth and development. The new and distinct cultivar of artichoke plant named 'PS-MSC0006' is characterized by:

1. male sterility;
2. fleshiness of bracts;
3. fleshiness of hearts;
4. uniformity of head shapes;
5. compact, reduced plant height; and
6. reduced spinosity on bracts.

DETAILED BOTANICAL DESCRIPTION

The following observations, measurements and values describe plants of 'PS-MSC0006' grown in Chowchilla, Calif. under conditions which closely approximate those generally used in horticultural practice. Chowchilla is located in California's central San Joaquin valley. Conditions can vary greatly during the summer months. Air temperature can range between the low 20's (degrees Fahrenheit) in the winter to well above the 100 (degrees Fahrenheit) during the summer months. Relative humidity is generally low with values ranging from the mid 40's to the high 60's. Prevailing winds are westerly and rainfall rarely exceeds 15" (inches) of rainfall.

The date of first harvest is approximately May 30 and the date of final harvest is approximately June 17, depending on environmental conditions. Plant growth from November to February is moderate, depending upon environmental and agronomic conditions. Plant growth and development from March to June is rapid, depending upon environmental and agronomic conditions, with sexual stages initiating in late April.

All color references below are measured against The Munsell Book of Color, Munsell Color MacBeth Division of Kollomorgen Corporation. Colors are approximate as color depends on horticultural practices such as light level and fertilization rate, among others.

The age of the plants described is approximately 349 days (229 days from transplanting and an additional 120 days developed in transplant trays).

Parentage:

*Female parent.*—CTC6 (seed parent).

Classification:

*Botanical.*—*Cynara scolymus* L.

*Commercial.*—Artichoke c.v. PS-MSC0006.

Propagation: Asexual propagation either by tissue culture (standard micropropagation methodology) or division.

Plant:

*Height.*—x=81.28 cm. range=58.42–83.82 cm.

*Growth habit.*—Upright.

*Dimensions.*—x=81.28 cm (h)×157.48 cm (w). range: 58.42–83.82 cm (h)×142.24–177.80 cm (w).

*Side shoots.*—x=1.00. range: (none).

*Foliage density.*—Open, upright form give foliage density a moderately dense appearance.

*Side shoot development.*—Poor side shoot development.

*Length of side shoots.*—Between 14.6–23.5 centimeters.

*Diameter of side shoots.*—Between 2.8–4.2 centimeters.

*Number of leaves on side shoots.*—4–6.

*Main stem.*—Length of main stem: Between 27–46 cm. Diameter of main stem: Between 3.5–6.2 cm.

*Number of leaves on main stem.*—16–24.

*Capitulum.*—Size: Primary: 36.20–40.64 cm. Secondary: 26.04–27.94 cm. Shape:Oval. Some shape variability observed oval/spherical. Number: x=3.70/plant. Range: 2.0–6.0 heads/plant. Texture: intermediate, smooth. Fragrance: mild, lightly aromatic. Bract Size: x=6.88 cm (l)×6.14 cm (w). Range: 6.53–7.1 (cm) (l)×6.03–6.36 (cm) (w). Bract Shape: Bracts are predominantly oval shaped. Bract Texture: smooth, slight texture. Bract Number: x=51.50 bracts. Range: 50–54 bracts. Bract Color: Inner: 10 Y 9/4–10 Y 9/6, 8.5/6. Outer: 5 GY 8/4, 5 GY 7/6, 2.5 GY 8/6. Bract Basal Thickness: x=5.83 mm. Range: 4.0–6/0 mm. Heart Description: Concave, full well developed heart, thick bract connections. Heart Color: 10 Y 9/2, 10 Y 9/4. Papus Length: x=8.60 mm. Range: 7.0–10.0 mm. Papus Color: variable white coloration. Overall Cold Storage Response: Good cold storage response. Stems slightly browned, no blackening visible. Head Firmess: Heads are firm. Bract tips split "slightly" when squeezed. Bract Firmness: Bracts have same flexibility. This flexibility gives the bracts a malleable quality. Gloss: Dull appearance. Heads and outer bract's appearance is dull flat green, yellow color. Cold Storage (bold quality): Good heads remain firm and free of decay. Head Exerior (oxidation): Head exterior becomes only lightly oxidized, not blackened. Juiciness: Moderate presence, some exudate is visible following stems cuts. Head Response (weather): No adverse responses to various weather conditions were observed on head (capitula) or plant tissue. Bud Burst: Between May 10–June 15. Bud Weight: Between 535.45 and 562.15 grams; average 550.83 grams per head. Bloom Time: Between June 1–June 20. Bloom Duration: Approximately 40 days. Bloom Depth: 9–11 cm. Bloom Shape: Head (slightly globose). Floret Number per Bloom: 835–962. Floret Size: between 5.8–7.0 cm in length; between 1.7–2.0 in width. Floret Color: Between 10PB 7/6–10PB 6/10–10PB 6/8–10PB 5/8.

*Seeds.*—Shape: Broad ovate. Size: 0.6–0.8 mm in length; 0.3–0.5 mm in width. Number: Highly variable between 30–1382; average 520 seeds per head. Color: Light brown hues with dark speckling.

*Foliage.*—Shape: Irregularly dentate, pinnatisect, tomentose and mucronulate. Length: x=97.88 cm. Range: 92.0–107.2 cm. Width: x=59.72 cm. Range: 54.1–67.4 cm. Leaf Serrations: x=31.72 mm. Range: 24.0–40 mm. Leaf Basal Angle: x=29.08 degrees. Range: 20–40.0 degrees. Leaf Ratio (L/W): x=1.60. Range: 1.05–1.86. Leaf Area: x=5,758.22 $cm^2$. Range: 5,112.72–7083 $cm^2$. Color: 5 GY 4/4–5 GY 4/6; 2.5 GY 4/6. Texture: Moderate, rough. Leaf has a soft non-uniform blistered quality (raised regions vary in size). Veination: Intermediate, greenish coloration. Midvein is white and prominent. Pubescence: Smooth most leaf surfaces are smooth. Some sparse pubescence is visible. Leaf Basal Thickness: x=24.77 mm. Range:20.0–35.0 mm. Leaf Distance Between Serrations: x=45.98. Range:35.0–60.0 mm. Petiole Length: x=13.51 cm. Range: 10.4–17.1 cm. Petiole Width: $\bar{x}$=5.73 cm–5.73 cm. Range:4.0–6.8 cm.

Disease resistance: No observations made.

General observations: This new artichoke cultivar is a unique type that exhibits the following characteristics.

Male sterility, a unique trait that is easily identified during flowering stages. The absence of pollen on most florets during anthesis (flowering) is unique with an estimated 5% of the florets shedding a very small volumes of pollen. These pollen volumes are poorly represented and difficult to detect.

The plants are extremely short in height. Ranging from 58–83 cm. Its comparative head qualities to California's artichoke variety Green Globe include: thick fleshy hearts (receptacles), oval shape and green (non-glossy) exterior coloration. These non-glossy heads (capitula) are large. Producing an average size (10–12) primary, size (36) secondaries and size (60) tertiaries. Head numbers range between 2–6 heads per plant.

Floral stalk development and head numbers can vary. Anthocyanin coloration is visible, but only in the innermost, immature bracts. This presence would be characterized as light and its presence can vary. The head spinosity is moderate to light. The average spine length varies between 0.5 and 2.0 mm. The plants upright growth habit is compact, but growth is vigorous. The canopies coloration is a medium green/yellow color ranging from lighter to darker shades. These colors range on the Munsell Leaf Color Chart 5 GY 4/4–5 GY 4/6, 2.5 GY 4/6. Leaf spinosity is moderate, categorized as few. Floral stalk development during anthesis produces a purple flower. Flower color varies only with flower maturity. The phenotypic characteristics may vary slightly, depending upon variations in environmental factors. Including weather (temperature, humidity and light intensity), day length, soil type, farming practices, location and time of year.

I claim:

1. A new and distinct cultivar of artichoke plant named 'PS-MSC0006' as described and illustrated herein.

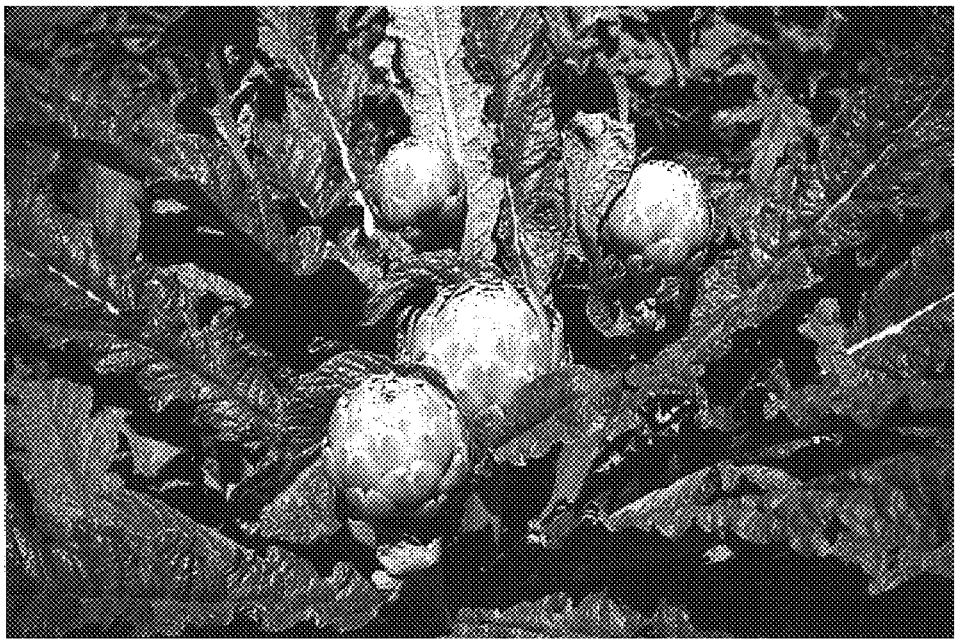

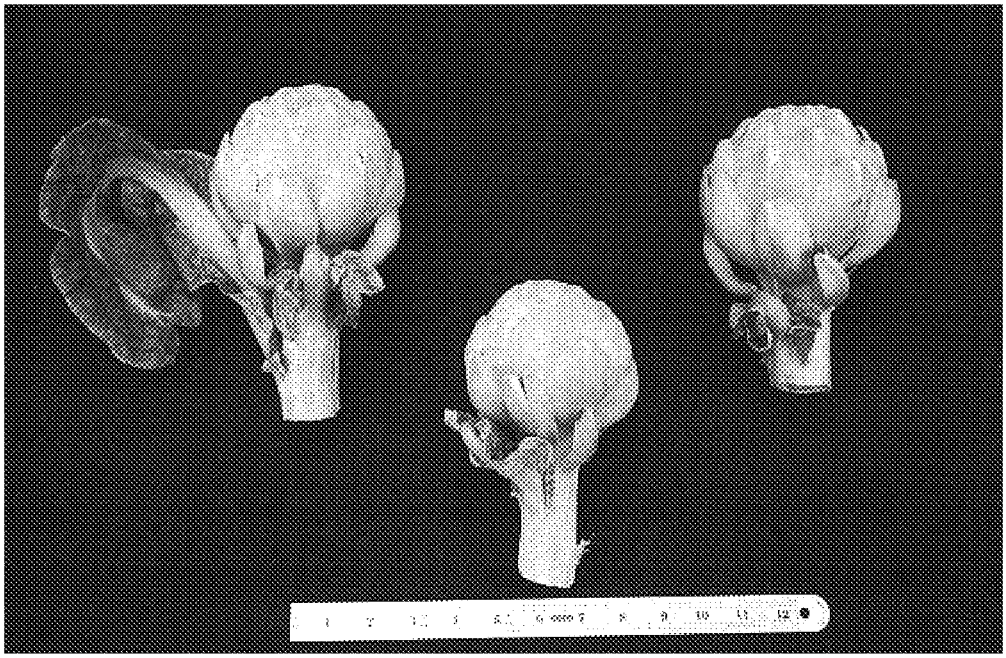

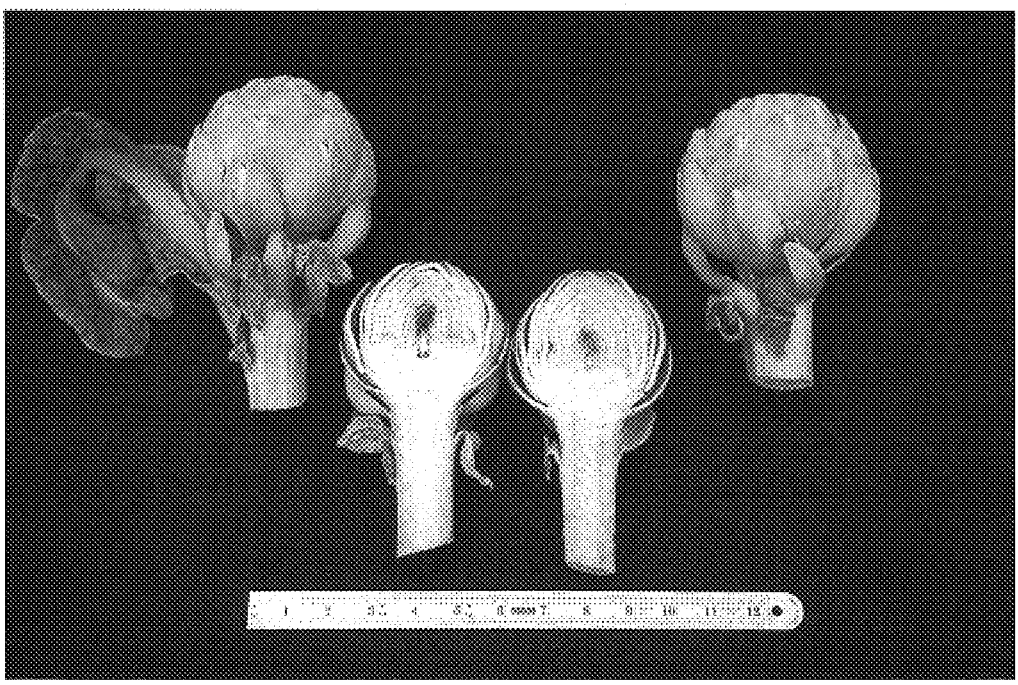

* * * * *